United States Patent [19]

Malcosky

[11] Patent Number: 4,658,750
[45] Date of Patent: Apr. 21, 1987

[54] APPARATUS AND METHOD FOR DETECTING GAS BUBBLES IN WATER, AND APPARATUS FOR HANDLING AN OCEANOGRAPHIC DEVICE

[75] Inventor: Norman D. Malcosky, Columbus, Ohio

[73] Assignee: Columbia Gas System Service Corp., Columbus, Ohio

[21] Appl. No.: 806,386

[22] Filed: Dec. 9, 1985

Related U.S. Application Data

[62] Division of Ser. No. 475,591, Mar. 14, 1983, Pat. No. 4,571,984.

[51] Int. Cl.⁴ .............................................. B63G 8/42
[52] U.S. Cl. ................................... 114/244; 114/242; 114/249; 114/366
[58] Field of Search ............... 114/244, 242, 249, 250, 114/365, 366, 368, 377

[56] References Cited

U.S. PATENT DOCUMENTS 3,005,973 10/1961 Kietz .
3,214,728 10/1965 Higgins .
3,541,717 11/1970 Grayson .
3,713,083 1/1973 Hunnicutt, Jr. .
3,992,923 11/1976 Roberts .
4,001,764 1/1977 Holland et al. .
4,063,212 12/1977 Sublett .
4,130,010 12/1978 Wonn .
4,305,140 12/1981 Massa .

FOREIGN PATENT DOCUMENTS 1231486 5/1971 United Kingdom ................ 114/244
1522131 8/1978 United Kingdom ................ 114/244

Primary Examiner—Joseph F. Peters, Jr.
Assistant Examiner—Paul E. Salmon
Attorney, Agent, or Firm—Sidney W. Millard

[57] ABSTRACT

The invention provides a side scanning sonar apparatus for detecting gas bubbles in water. This apparatus transmits low frequency sonar signals horizontally through the water and detects the resultant echoes. The echoes due to bubble columns can be discriminated from those due to simple reflection from solid objects. The invention also provides a special handling apparatus to permit launching and recovery of a towed sonar apparatus in which the upper part of the fairing is relatively fragile.

10 Claims, 7 Drawing Figures

APPARATUS AND METHOD FOR DETECTING GAS BUBBLES IN WATER, AND APPARATUS FOR HANDLING AN OCEANOGRAPHIC DEVICE

This application is a division of Ser. No. 475,591, filed Mar. 14, 1983, now U.S. Pat. No. 4,571,984, granted Feb. 25, 1986.

BACKGROUND OF THE INVENTION

The invention relates to an apparatus and method for detecting gas bubbles in water. The invention also relates to a handling apparatus designed for the recovery, launching and storage of an oceanographic device with a thin, non-self supporting "skin" or fairing.

It has been known for some time that underwater natural gas deposits leak small amounts of natural gas into the overlying water, the natural gas rising to the surface in the form of small bubbles; thus, it is desirable to be able to detect rising columns of such bubbles in water in order to locate sites which are likely to contain gas deposits. Some of these columns of bubbles can be detected visually on the surface as the bubbles break, but such visual observations are effectively confined to very calm conditions since even small waves on the surface render such visual observations effectively impossible. The rising columns of bubbles have also been detected by downward-looking active sonar apparatus. (The terms "active sonar" and "passive sonar" are used herein with their conventional meaning in the art, an active sonar apparatus being one which itself radiates fluid wave energy into the surrounding water and detects echoes caused by this fluid wave energy being reflected back from objects in the water, while a passive sonar system does not itself radiate fluid wave energy but merely listens for any noises present in the water).

A typical prior art active sonar system capable of detecting bubbles of gas or liquid rising through water is described in U.S. Pat. No. 4,001,764 issued Jan. 4, 1977 to Holland et al. This prior art apparatus comprises a submersible, torpedo-shaped device which radiates a sonar beam downwardly and which is towed by a boat, this boat containing recording and other apparatus for interpretation of the sonar signals. The apparatus is intended for use in detecting leaks from submerged pipelines and the method used is a comparative one; the device is towed along the pipeline when it is known to have no leaks, and, after a leak develops, the device is towed along the pipeline and the two acoustical profiles thus generated compared.

Although in theory the Holland apparatus can be used to detect columns of bubbles rising from underwater natural gas deposits, its usefulness for this purpose is seriously impaired by the fact that the sonar beam is downward looking. Thus, only a narrow path directly below the towing boat is scanned at any one time, and the shallower the water in which the device is used the narrower the track scanned. Because of the very large areas of ocean bottom which have to be surveyed for natural gas deposits, it is customary in underwater survey work to survey with a spacing of about one-half mile between adjacent tracks, and the narrowness of the area scanned with the Holland apparatus would mean that deposits falling between tracks would be missed. If the spacing between adjacent tracks is made sufficiently small to ensure that the Holland apparatus does not miss any bubble columns, the areas of ocean bottom surveyed during a working day becomes too small to be practicable. Obviously, any sonar survey system utilizing a downward looking beam will suffer from the same problem.

A further problem with using the Holland apparatus is that, as already mentioned, it relies upon comparing acoustical profiles obtained when no bubbles are rising from the ocean floor and when bubbles are rising. If the apparatus is used to survey previously unchartered areas of ocean bottom for rising bubbles columns, it is of course impossible to produce the "no-leak" acoustical profile required for comparison purposes.

It might at first appear that the problem of limited surveying rate in the Holland and similar apparatus could be overcome by directing the sonar beam transversely of the apparatus instead of vertically downwardly. However, the Holland apparatus operates with a high-frequency beam (such beams typically have frequencies of around 60 kHz) and it has hitherto been necessary to use such high frequencies in detecting gas bubbles. Elementary wave theory shows that waves, including sound waves, will only be reflected by objects having dimensions greater than one-half the wave length of the wave. Since the rising gas bubbles from natural gas deposits are known to be only a few centimeters in diameter, while the velocity of sound in water is around 1,500 meters per second, those skilled in the art have hitherto believed that the use of high frequency sonar was imperative for detection of the small bubbles from natural gas deposits. However, high frequency radiated acoustical energy is much more rapidly attenuated in sea water than is low frequency acoustical energy, and for this reason even a side scanning high-frequency sonar apparatus capable of detecting rising columns of gas bubbles would have such a limited range that it would still not be practicable for surveying large areas of ocean bottom. Furthermore, when using such a side scanning apparatus considerable difficulty would be encountered in distinguishing rising columns of bubbles from other reflections due to fish or other objects in the water. A column of bubbles can be spotted relatively easily on a downward looking sonar trace because the spread of the bubbles through the water produces (on the conventional type of sonar plot which effectively plots depth of reflections against distance traveled by the apparatus) a characteristic trace showing reflections over a large vertical interval, as opposed to the sharp reflections at a particular depth caused by fish or other objects. On the other hand, a side scanning sonar beam would intersect the narrow vertical column of bubbles transversely and it is not immediately apparent how the reflection produced by this transverse intersection with a rising bubble column could be distinguished by the echo produced by any other small object.

There would also be problems involved in handling a side-scanning sonar apparatus. Conventional fluid wave energy transducers are of such a shape that they cannot be satisfactorily towed by themselves. Accordingly, the actual transducers which effect radiation and detection of fluid wave energy must be mounted within a streamlined casing or fairing to give good hydrodynamic qualities to the apparatus. The transducers will only radiate and detect fluid wave energy efficiently while they are immersed in water, so the fairing must flood while the apparatus is submerged in water. Also, to prevent excessive dissipation of fluid wave energy as the sonar beam passes through the fairing that part of the fairing through which the sonar beam passes must be made so thin that it is relatively fragile and is easily damaged during launching or retrieval of the apparatus. Providing an appropriately thin fairing does not present much difficulty in a downward looking sonar apparatus since the sonar beam only passes through the lower part of the fairing and thus a fairing can be used which has a relatively thin and fragile lower section and a relatively thick, rigid and strong upper section, all the manipulation and the handling of the fairing during launching and recovery being effected by manipulating the rigid upper part of the fairing. However, in a side scanning sonar apparatus, the sides of the fairing must be thin (in practice, a side scanning apparatus will always use two side scanning beams on opposed sides of the apparatus) and the handling of the resultant fragile fairing poses grave difficulties.

It will thus be seen that there is a need for a method and apparatus for rapidly scanning large areas of water to detect rising columns of gas bubbles therein. It will also be seen that there is a need for an apparatus capable of handling a sonar apparatus which uses a very fragile fairing. This invention seeks to meet both these needs.

SUMMARY OF THE INVENTION

This invention is based upon the discovery that it is possible to detect rising columns of gas bubbles using *low frequency* sonar apparatus by distinguishing between the type of "echoes" produced by gas bubbles and those produced by other objects. Furthermore, it has been found, it an appropriately shaped low-frequency, side scanning sonar beam is used, the necessary discrimination between bubble echoes and other echoes can be made from a plot produced using a conventional sonar plotting device with only minor modifications.

Accordingly, one aspect this invention provides a side scanning sonar apparatus for detecting gas bubbles in water comprising a body at least part of which is submersible in water, drive means for moving the body in one direction through the water, and orientation control means for maintaining the body in a predetermined orientation to the vertical. At least one fluid wave energy transducer is mounted on a submersible part of the body, this transducer being capable of emitting a beam of low frequency fluid wave energy substantially, horizontally and transversely of the direction in which the drive means moves the body. The beam emitted from the transducer must have a width of at least about 45° in a horizontal plane and the transducer must also be capable of detecting low-frequency wave fluid energy impinging thereon.

In another aspect, this invention provides a method for detecting gas bubbles in water which comprises radiating a pulse of fluid wave energy into the water, this fluid wave energy being of low frequency and being radiated substantially horizontally through the water, after the pulse has terminated detecting fluid wave energy in the water, and supplying a signal representative of the detected fluid wave energy to a discrimination means capable of discriminating between signals produced by passive reflection of the radiated fluid wave energy and signals produced by secondary emission of fluid wave energy from resonant structures activated by the radiated wave energy.

To overcome the problems described above in the handling of fragile oceanographic sonar devices, the invention provides an apparatus for handling a fragile oceanographic device comprising a base member, an arm mounted on the base member and pivotable relative thereto about a substantially horizontal axis and a clamping assembly mounted upon the arm at a point spaced from the base member. This clamping assembly is pivotable relative to the arm about a substantially horizontal axis and is provided with clamping means movable between a locked position, wherein the clamping means clamps the device, thereby preventing relative movement between the device and the clamping assembly, and an unlocked position, wherein the clamping means does not clamp the device, thereby permitting relative movement between the clamping assembly and the device.

Finally, this invention provides in combination, a towable oceanographic device and a towing vessel therefore, the oceanographic device having a fairing and a cable attachment member projected upwardly from this fairing, and the towing vessel having mounted thereon a winch and handling apparatus. This handling apparatus comprises an arm pivotally mounted on the vessel for pivotable movement relative thereto about a substantially horizontal axis and a clamping assembly mounted upon this arm at a point spaced from the point at which the arm is mounted on the vessel. The clamping assembly is pivotable relative to the arm about a substantially horizontal axis and is provided with a clamping means movable between a locked position, wherein the clamping means clamps the cable attachment member of the oceanographic device, thereby preventing relative movement between the oceanographic device and the clamping assembly, and an unlocked position, wherein the clamping means does not clamp the cable attaching means, thereby permitting relative movement between the clamping assembly and the oceanographic device. Naturally, a cable is provided connected between the winch on the vessel and the cable attachment member on the oceanographic device.

DETAILED DESCRIPTION OF THE INVENTION

Figure 1:
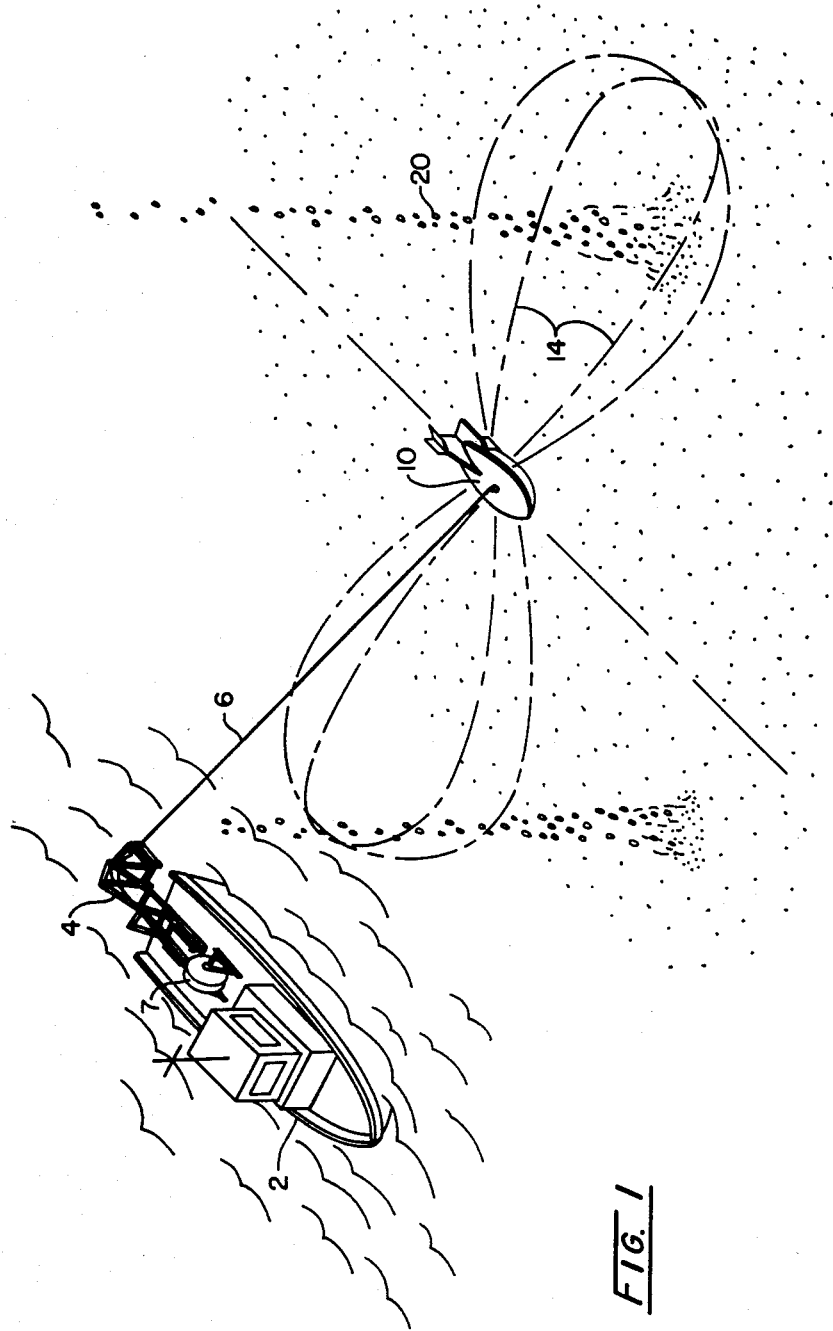
FIG. 1 shows schematically a sonar apparatus of the invention and its towing vessel being used to survey a section of sea bottom.

The body of the instant sonar apparatus must be at least partially submersible in water and the transducer of the apparatus must, for obvious reasons, be mounted on a submersible part of the body so that it will lie underwater when the apparatus is in use. Although the instant sonar apparatus could have the form of a surface ship with the transducer mounted below the water line, it is preferred that the instant sonar apparatus be in the form of a completely submersible vessel. Also, although the instant sonar apparatus could be in the form of an independent, self-propelled submersible vessel, it is preferred that the instant sonar apparatus be in the form of a non-self-propelled vessel which is towed from a boat or ship, i.e. that the drive means of the sonar apparatus be in the form of a cable attachment member to which a cable can be attached so that the apparatus can be towed.

In order that the instant sonar apparatus can project its sonar beam substantially horizontally, it is obviously necessary that the apparatus when in use be maintained at a proper orientation to the vertical. Any appropriate form of orientation control means may be used for this purpose. For example, if the instant sonar apparatus is in the form of a surface vessel, the hull design of the surface vessel will act as the orientation control means. The orientation control means of a submersible instant sonar apparatus may be in the form of movable hydroplanes. However, in the preferred form of sonar apparatus comprising a towed submersible vessel, appropriate control of the vessel's orientation can be affected by providing the vessel with a cable attachment member which projects upwardly from a hydrodynamically streamlined fairing forming the main part of the vessel; in such a vessel the towing cable extends above the vessel and automatically maintains proper orientation. The vessel is also desirably provided with one or more fins to assist in maintaining proper orientation.

The transducer used in the instant sonar apparatus must be capable of both radiating and detecting fluid wave energy. Although if desired, the transducer may comprise separate radiating and detecting elements, it is usually more convenient (as those skilled in the art are aware) to use a single transducer element capable of both radiation and detection. As described in more detail below, a transducer capable of providing the beam shape necessary in the instant sonar apparatus can readily be constructed from conventional, commercially-available transducer elements.

The fluid wave energy emited by the transducer of the instant sonar apparatus, and used in the instant detection method must be of low frequency, the term "low frequency" being used in its normal sonar sense to mean frequencies below about 10 kHz. Although the optimum frequency may vary somewhat depending somewhat upon sea conditions or other factors, very desirably the low frequency is in the range of 2–5 kHz.

As mentioned above, those skilled in the art have hitherto believed that detection of natural gas bubbles having diameters of only a few centimeters in water necessitates the use of high-frequency sonar. I have discovered, however, that not only do small natural gas bubbles respond to low-frequency sonar despite the fact that the diameter of the bubbles is considerably less than half the wave length of the low frequency sonar beam, but that the bubbles produce a very characteristic form of response which can readily be distinguished from the normal type of response caused by simply reflection of the beam from other objects. It appears that the impingement of the low frequency beam upon the gas bubbles causes the gas bubbles to resonate at their natural frequency of vibration, whereupon the vibrating bubbles act as secondary sources of fluid-wave energy. Because the bubles continue to vibrate for a considerable period, the response produced from a bubble stimulated by a short pulse of fluid wave energy lasts much longer than does the response from simple reflection of the pulse of fluid wave energy from a solid object. The difference in the length of response between bubbles and other objects makes it possible to differentiate between gas bubbles and other object.

The means used to effect discrimination between the signals produced by secondary emission of fluid-wave energy from the gas bubbles and passive reflection of the radiated fluid-wave energy from other objects may be any apparatus capable of measuring length of response time to an accuracy of the order of milliseconds. Thus, at least in theory, the necessary discrimination could be effected by arranging for a response to be displayed upon a cathode ray oscilloscope and measuring the response time thereon. Similarly, sophisticated electronic data processing equipment could be used to measure length of response time. However, it has been found that, if a proper beam geometry is employed, the necessary discrimination can readily be achieved using a conventional sonar plotting apparatus of the type normally used to produce a bottom profile when using a downward looking sonar apparatus. In such a plotting apparatus, one axis (rectangular axes are normally employed) measures time (since the sonar apparatus is normally being moved at a steady speed during plotting, this axis in effect also represents distance traveled by the sonar apparatus), while the other axis measures time between the termination of the last sonar pulse transmitted and the receipt of the response detected. If one uses a beam having a width of at least about 45° in a horizontal plane, the responses produced by gas bubble columns have the very characteristic form shown in FIG. 7 of the accompanying drawings. This characteristic shape, which may be referred to as a "smeared parabola" comprises the area between a "V" having its vertex pointed towards the zero of the axis representing elapsed time since the last pulse and a substantially parabolic curve disposed within and pointing in the same direction as the "V". The parabolic shape is caused by the fact that as the sonar apparatus is towed past a single rising column of bubbles, the range to the bubble column is greatest when the bubble column first comes within the operable range of the side-scanning beam, descreases to a minimum as the track of the sonar apparatus passes its closest point to the bubble column and then increases again after the sonar apparatus has passed this point until the bubble column passes out of range of the sonar beam. The width of the smeared parabola parallel to the "time since last pulse" axis of the plot is due to the period of time which the bubble resonates; this elongation of the trace along this axis is comparable to the effect produced on a radar screen by an aircraft which carries an active transponder which emits a response immediately following the normal radar echo. It will be apparent that the actual location of the bubble column will be at the vertex of the "V" shape.

Since the natural frequency of vibration of a gas bubble (and thus the frequency of the fluid-wave energy which must be applied to the gas bubble to cause a perceptible resonance thereof) varies with the diameter of the gas bubble, and since a single bubble rising several hundred feet through water expands to many times its original diameter before it reaches the surface due to the changes in hydrostatic pressure with depth, it is surprising that detection of bubble columns can be consistently effected using fluid-wave energy of one given frequency. However, it has been discovered that a very large proportion of natural gas bubbles rising in water even from great depths have a diameter in the range of 1–3 centimeters; it appears that once a bubble exceeds about 5 centimeters in diameter, it tends to break into a multiplicity of smaller bubbles, thus maintaining the majority of bubbles within the diameter range of 1–3 centimeters regardless of depth. Accordingly, use of fluid-wave energy within the range of 2–5 kHz gives good results.

It has also been discovered that the shape of the beam emitted by the instant sonar apparatus, and thus the shape of the transducers used to produce the beam, are important in obtaining good results. Preferably, the instant sonar apparatus produces a beam having a width in the horizontal plane of about 90° with the center of the beam directed substantially normally to the direction in which the drive means moves the body of the sonar apparatus, and also preferably the angular width of the beam in the vertical plane is not more than about half of the beam in horizontal plane. Transducers used in sonar apparatus are conventionally piezoelectric devices with a single radiating face which vibrates to produce the beam of fluid-wave energy. As those skilled in the art are aware, the angular width of the beam produced by such transducer in any given direction is inversely proportional to the length of the transducer in that direction; thus, to produce the preferred beam of the instant sonar apparatus, the ratio of the vertical height of the transducer to its horizontal length parallel to the direction in which the sonar apparatus moves is desirably at least about 2:1. It has been found that using a beam having angular width of about 90° in the horizontal plane and 45° in the vertical plane gives good results; such a beam is capable of detecting bubble columns at distances of up to about 1,000 feet (about 300 meters) from the track of the vessel but does not suffer excessively from surface effects caused by the sonar beam intersecting the surface. Using a beam which is too narrow in the horizontal plane gives plots which are difficult to interpret; for example, experiments have been conducted using a transducer having a vertical height:horizontal length ratio of 4:1, but the traces produced by such apparatus have the form of very sharp "V" and are difficult to interpret.

FIG. 1 of the accompanying drawings shows a sonar apparatus of the invention being towed by a boat and being used to survey a section of ocean for columns of gas bubbles. The towing boat 2 is provided with an instant handling apparatus 4; a towing cable 6 extends from a winch 7 through a cable guide member (described in more detail below) incorporated in the handling apparatus and thence downwardly to the sonar apparatus 10 which is of the totally submersible type and which is being towed by the boat 2 along a straight track, preferably at as uniform a speed as possible. The cable 6 not only effects towing of the sonar apparatus 10 but also carries electrical connections between the sonar apparatus and various auxiliary apparatus (described in more detail below) used to power and interpret the results obtained by the sonar apparatus. As described below, the cable 6 may itself be faired to reduce hydro-dynamic drag thereon. The sonar apparatus 10 is shown in FIG. 1 emitting two sonar beams 14, these beams being directed horizontally and normally to the track of the sonar apparatus 10 in opposed directions. The envelope of each beam 14 has a width in the horizontal plane of approximately 90° and a width in the vertical plane of approximately 45°; thus, each beam 14 extends 45° ahead and 45° behind the beam of the sonar apparatus 10. Each beam 14 is shown intersecting a rising column 20 of natural gas bubbles leaking from gas bearing strata on the ocean bed.

Figure 2:
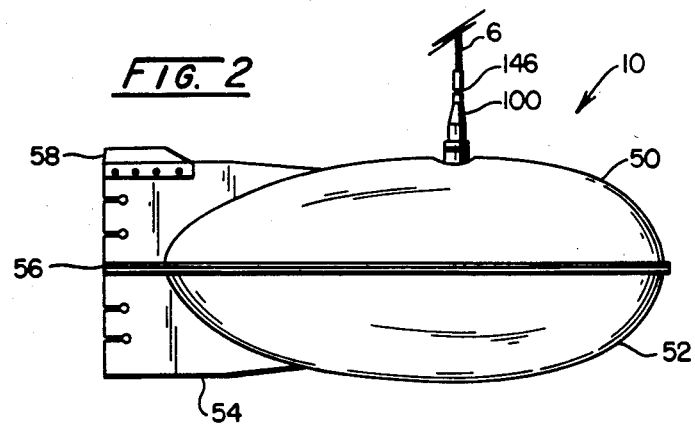
FIG. 2 is a side elevation of the sonar apparatus shown in FIG. 1.

The external form of the sonar apparatus 10 is shown in FIG. 2. As shown in that figure, the sonar apparatus 10 has a hydrodynamically streamlined fairing comprising an upper fairing 50 and a lower fairing 52, each of which is substantially hemi-ellipsoidal in shape so that the complete fairing is substantially ellipsoidal having its longest axis along the direction in which it is towed. The presently preferred from of fairing has substantially the form of a prolate ellipsoid of revolution having a major axis:minor axis ratio of 3:1. Since, as described below, fluid-wave energy beams must pass through both the sides and the underpart of the fairing, both upper and lower fairings must be formed of a thin material which does not cause unacceptable interference with the beams; they may, for example, be formed of acrylonitrile-butadiene-styrene (ABS) plastic or a composite of vinyl esteresins and fiberglas cloth with a maximum thickness of approximately ⅛ inch 3 mm.) Thus, in contrast to a conventional downward-looking sonar apparatus, in which the fluid-wave energy beam only passes through the underpart of the fairing, and thus in which the upper fairing can be made thick-walled so as to be supported against a support structure when it is retrieved onto the ship by pulling the entire apparatus against that support structure, the instant apparatus has its entire fairing made thin-walled and fragile. Consequently, the fairing is not capable of supporting the entire weight of the vehicle or capable of resting against a conventional support structure on the vessel. Accordingly, handling of the instant apparatus has to be effected using the special type of handling apparatus of the invention described below.

At the rearward end of the fairing, the apparatus is provided with a fin assembly comprising a horizontal fin 56, a vertical fin 54 and an auxiliary fin 58 which extends outwardly in both directions from, and slightly upwardly from the upper horizontal edge of the vertical fin; thus, the auxiliary fin 58 is of the dihedral type.

A cable attachment member 100 projects vertically upwardly from the upper fairing 50 and lies in the vertical plane of symmetry of the fairing. This cable attachment member 100 has the cable 6 attached thereto, while the cylindrical portion of the cable attachment member 100 lying adjacent the cable 6 has a groove 146 machined in its cylindrical surface. The fins 54, 56 and 58 and the cable attachment member 100 are preferably made of type 316 stainless steel to provide the necessary corrosion resistance against salt water.

The placement of the cable attachment member projecting from the upper part of the fairing 50 (the center of gravity of the apparatus lies almost directly below the cable attachment member 100), together with the fins 54, 56 and 58 provide the necessary orientation control means to keep the apparatus in a proper orientation to the vertical and also serves to keep the apparatus at a constant depth. Once the apparatus has been deployed at the appropriate depth, which is usually from 20 to 50 feet (6 to 15 meters) the apparatus 10 is towed by the boat 2 (FIG. 1) and the towing force is thus exerted at the upper end of the cable attachment member 100. The moment of this towing force about the center of gravity of the apparatus tends to force the nose of the apparatus downwardly into a diving position. However, once the nose of the apparatus is thus tipped downwardly, the water flowing over the apparatus will tend to impinge upon the upper faces of the fins 56 and 58, thus providing an appropriate countermoment which tends to lift the nose of the vehicle. The combined effect of these two opposing moments holds the apparatus in a stable position wherein it does not dive nor surface but maintains a substantially constant depth. It has been found that by the aforementioned placement of the cable attachment member 100 and the use of the fins 56 and 58 in the form shown, the apparatus can be made to run at constant depth indefinitely. The appropriate vertical orientation of the apparatus is largely maintained by the vertical component of the tension in the cable 6; since, as described below, the fairing floods during towing, the apparatus becomes heavier than water and its weight is partially supported by the vertical component of the tension in the cable 6. Thus, since the center of gravity of the apparatus lies below the cable attachment member 100, the apparatus will maintain a proper vertical orientation during towing.

Figure 3:
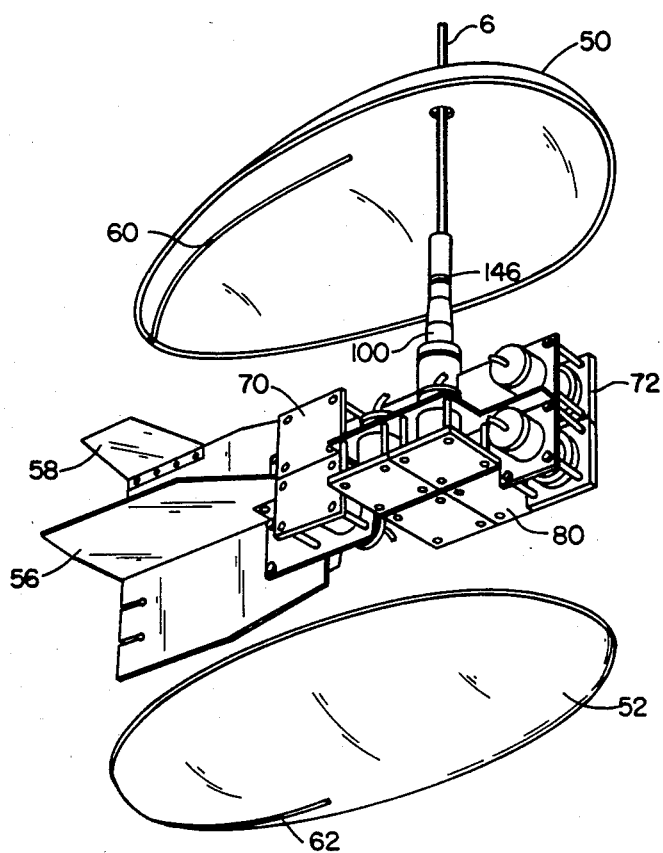
FIG. 3 is an exploded perspective view from in front, underneath and to one side of the sonar apparatus shown in FIGS. 1 and 2.

The internal structure of the apparatus 10 can be seen in FIG. 3. As shown in that figure, slots 60 and 62 are cut in the upper and lower fairings 50 and 52 respectively, these slots extending in the vertical planes of symmetry in the upper and lower fairings from the rear ends of the fairings and accommodating for the upper and lower parts of the vertical fin 54. The slots 60 and 62 are not sealed against entry of water and thus the internal chamber within the fairing floods when the apparatus 10 is submerged; this flooding is assisted by leakage between the adjacent edges of the upper and lower fairings 50 and 52 respectively, which are only loosely fastened to one another, and by leaking of water through the aperture by means of which the cable attachment member passes through the upper fairing 50. This flooding of the fairing is necessary to ensure that the various transducers disposed within the fairing are immersed in water, as is necessary for their proper operation.

As shown in FIG. 3, the fairing accommodates three separate transducers, namely a starboard transducer 70, a port transducer 72 and a downward-looking transducer 80. The transducers 70, 72 and 80 are all formed by assembling conventional piezo-electric transducers having square radiating faces; each of the transducers 70 and 72 comprises two of the square transducers disposed one above another, while the downward-looking transducer 80 comprises a 2×2 array of transducers. Thus, each of the transducers 70 and 72 has a vertical height:horizontal length (in the towing direction) ratio of 2:1. As already mentioned, this produces a sonar beam having a width of approximately 90° in a horizontal plane and 45° in a vertical plane, the center of the beam being directed normally to the track of the apparatus 10. Obviously, the starboard transducer 70 produces the starboard beam 14 shown in FIG. 1 while the port transducer 72 produces the port beam shown in FIG. 1. The downward-looking transducer 80 (the beam from this transducer is omitted from FIG. 1 for the sake of clarity) serves as a sub-bottom profiler and acts in the same manner as a conventional sub-bottom profiler. The transducer 80 will detect bubble columns close to the track of the apparatus 10 and is thus useful in relatively deep water where the sonar beam can cover a relatively large area on either side of the track. The transducer 80 also acts as a fathometer to determine the depth of water below the vessel and thus cooperates with the navigational system of the boat 2 (FIG. 1) to locate bubble columns. For the reasons already mentioned, the transducer 70, 72 and 80 operate on the frequency range of 2–5 kHz since this is the optimum range for detecting gas bubbles.

Electrical connections between electrical lines (not shown) running within the cable 6 and the transducers are made by a water-tight, epoxy-potted connector at the lower end of the cable connection member 100. In the form shown in FIG. 3, the apparatus weighs approximately 410 lbs. (approximately 186 kg.). If desired, additional equipment may be included in the apparatus 10, for example a depth indicator, pressure sensor, conductivity cell for salinity measurements, temperature monitor, television camera, water sample pump or any other instrumentation useful in oceanographic surveying.

Figure 4:
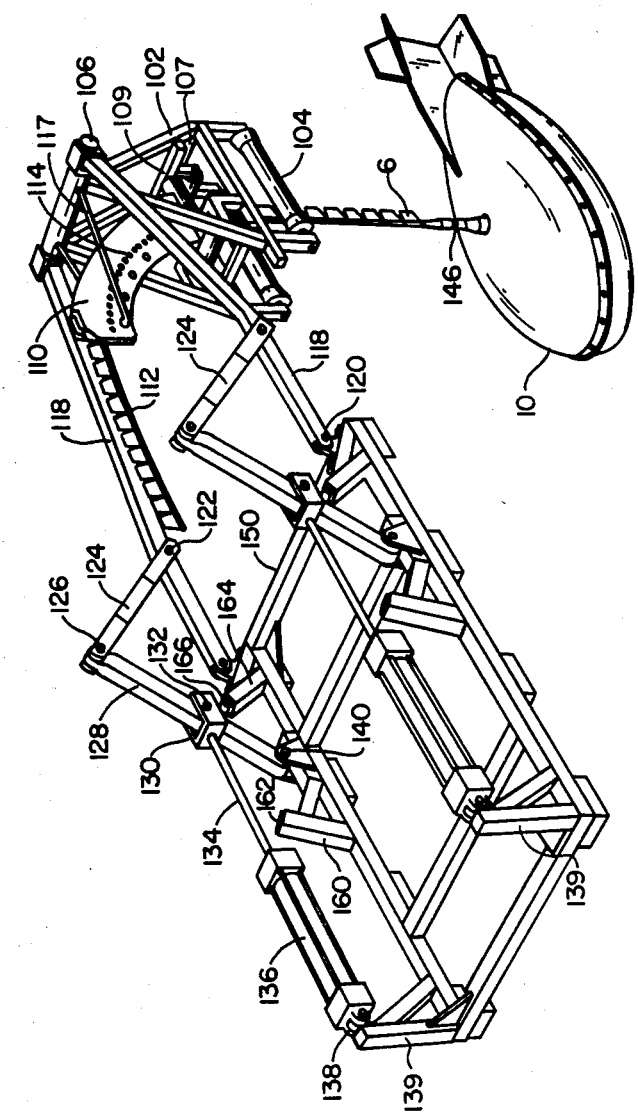
FIG. 4 is a perspective view of the sonar apparatus shown in FIGS. 1-3 and the handling apparatus therefore.
Figure 5:
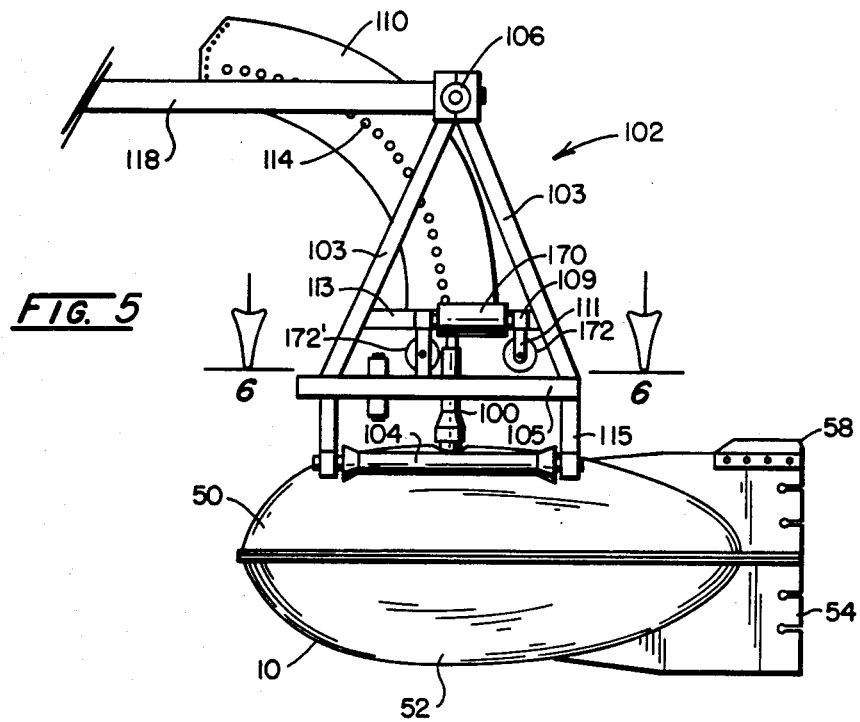
FIG. 5 is a side elevation of the sonar apparatus and the clamping means of the handling apparatus shown in FIG. 4, with the clamping means in its locked position.
Figure 6:
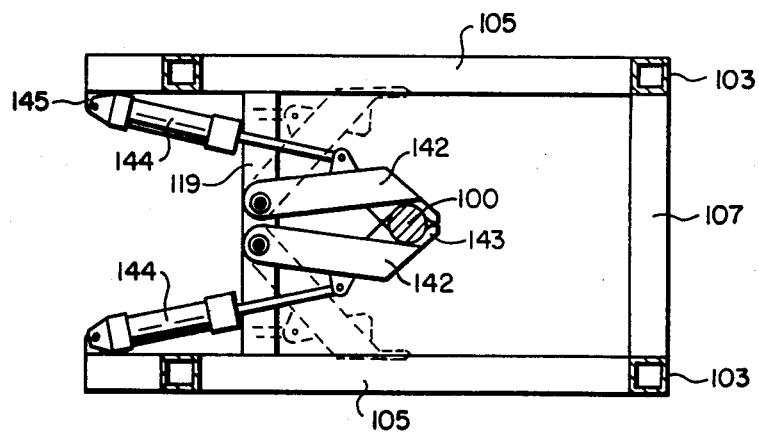
FIG. 6 is a section along line 6—6 in FIG. 5 with certain parts omitted for clarity.

FIGS. 4, 5 and 6 show in more detail the handling apparatus 4 shown in FIG. 1; the winch 7 is omitted from FIG. 4 for the sake of clarity. This handling apparatus comprises a base member having the form of a framework 150 which (as shown in FIG. 1) is fixedly mounted upon the afterdeck of the boat 2 so as to permit the apparatus 10 to be launched and retrieved over the stern of the boat 2. The framework 150 has projecting upwardly therefrom pairs of front and rear stop members 160 and 164 respectively, the upper ends of these stop members being provided with pads 162 and 166 respectively. The handling apparatus further comprises an arm assembly in the form of two "A" frame arms; each of these arms comprises a rearward member 118 pivotally mounted at 120 on the rear edge of the framework 150, a forward member 128 pivotally mounted at 140 on a portion of the framework 150 lying between the stop members 160 and 162, and a central connecting member 124, the forward end of this central member being pivotally mounted at 126 on the upper end of the associated forward member 128, while the rearward end of the central member 124 is pivotally mounted at 122 on the associated rearward member 118. A hydraulic piston-and-cylinder assembly having a piston rod 134 and a cylinder 136 is connected between each forward member 128 and a column 139 upstanding from the forward end of the framework 150; each cylinder 136 is pivotally mounted on the associated column 139 by a clevis and pin arrangement 139, while each piston rod 134 is pivotally connected to the associated forward member 128 of the "A" frame at 132 via a clevis 130. The hydraulic piston-and-cylinder assemblies 134, 136 enable the arm assembly 118, 124, 128 to be moved between a launching and retrieval position (as shown in FIG. 4) in which the forward members 128 are in contact with the pads 166 on the stop members 164, so that the rear ends of the members 118 extend well clear of the stern of the boat 2 (FIG. 1) thus enabling launching and retrieval of the fish, and a stowage position, in which the forward members 128 rest against the pads 162 on the stop members 160, so that the rearward members 118 assume a substantially vertical position and the whole arm assembly lies above the stern deck of the boat 2.

A clamping or saddle assembly 102 is suspended from the rearward end of the members 118, the saddle assembly 102 being freely pivotable relative to the members 118 around a pivot pin 106, so that the saddle assembly 102 can retain the same orientation to the vertical as the arms 118 are moved between their launching and retrieval and stowage positions by the hydraulic pistonand-cylinder assemblies 134, 136. As shown in FIGS. 4 and 5, the saddle assembly comprises two triangular frameworks, one lying adjacent each member 118; each triangular framework comprises two downwardly extending members 103 and a horizontal member 105 which interconnects the lower ends of the members 103. The two horizontal members 105 are interconnected at their rearward end by a horizontal brace 107 (FIG. 4). The rearward pair of downwardly extending members 103 are also interconnected by a brace 109, which carries two downwardly extending projections 111 (only the port side one of these projections 111 is visible in FIGS. 4 and 5), between which is rotatably mounted a roller 172. A similar roller 172' is rotatably mounted on a framework 113 interconnecting to the two horizontal members 105 and the forward pair of downwardly extending members 103. The axes of the rollers 172 and 172' extend parallel to the brace 107. A further pair of rollers 170 (only the port side one of which is visible in FIGS. 4 and 5) having axes parallel to the horizontal members 105 are rotatably mounted between the framework 113 and the brace 109. Finally, each of the horizontal members 105 has a pair of downwardly extending struts 115 disposed at its forward and rearward ends, and a roller pad 104 is disposed between the pair of struts 115 on each horizontal member 105.

The saddle assembly 102 further comprises a cable guide 110 which is supported at its upper end by rods 117 (FIG. 4) attached to the pivot pin 106 and at its lower end by the framework 113. The cable guide 110 has rotatably mounted therein a plurality of rollers 114, which are arranged on a 90° arc of a circle.

FIG. 6 shows apparatus provided in the saddle assembly 102 to provide for clamping of the cable connection member 100 on the apparatus 10. As shown in FIGS. 5 and 6, the two horizontal members 105 are interconnected intermediate their ends by a pair of horizontal braces 119 disposed above and below the horizontal members 105 (obviously, only the lower brace 119 is visible in FIG. 6). A pair of pincer arms 142 are sandwiched between and pivotally mounted on the two braces 119; each pincer arm 142 can be pivoted relative to the braces 119 by means of a hydraulic piston-and-cylinder assembly 144, which is connected between the associated pincer arm 142 and a lug 145 disposed at the forward end of the associated horizontal member 105. The hydraulic piston-and-cylinder assemblies 144 enable the pincer arms 142 to be pivoted between a locked position (shown in solid lines in FIG. 6) in which the pincer arms 142 clamp the cable connection member 100 of the apparatus 10, thereby preventing relative movement between the saddle assembly 102 and the apparatus 10, and an unlocked position (shown in broken lines in FIG. 6) in which the pincer arms 142 lie clear of the cable connection member 100. When the pincer arms 142 are in their locked position, projections 143 provided at their free ends enter into the groove 146 (FIGS. 2 and 3) to exclude any possibility of relative vertical movement between the apparatus 10 and the saddle assembly 102.

To effect launching of the apparatus 10, the hydraulic piston-and-cylinders 134, 136 are activated to move the arm assembly from its stowage position to its launch and retrieval position. When this movement has been completed, the arm assembly adopts the position shown in FIG. 4, with the forward members 128 in contact with the pads 166 on the stop members 164, but the apparatus 10 is still held relative to the saddle assembly 102 in the position shown in FIG. 5, the pincer arms 142 still engaging the cable connection member 100 and the roller pads 104 still being in contact with the upper fairing 50 of the apparatus 10. The rollers 114 on the cable guide 110 guide the cable 6 and its attached fairings 112 in a 90° arc so that the portion of the cable 6 adjacent the cable connection member 100 extends vertically upwardly from the cable connection member, while the portion of the cable extending from the upper end of the cable guide 110 to the winch 7 (FIG. 1) lies approximately parallel to the members 118. It should be noted that during this movement of the handling assembly to its launch and recovery position, with the pincer arms 142 engaging the cable connection member 100, no tension is maintained in the cable 6, the weight of the apparatus 10 being supported entirely by the pincer arms 142, and the upper fairing 50 being held only lightly in contact with the roller pads 104. If tension were applied to the cable at this point, the roller pads 104 might exert so much pressure on the fragile upper fairing 50 as to deform or damage the fragile upper fairing. Thus, the mode of support of the apparatus 10 is completely different from the conventional technique used with oceanographic devices having thick, robust upper fairings, which are simply drawn by cable tension into contact with appropriate pads. Also, it should be noted that, because the saddle assembly 102 is freely suspended from the pivot pin 106, movement of the handling apparatus from its stowage to its launch and retrieval position is accomplished without inverting the apparatus 10; again, this is necessary to avoid damage to the fragile fairing of the apparatus 10.

As best seen in FIG. 4, when the handling apparatus is in its launch and retrieval position, the members 118 extend horizontally or slightly downwardly from the boat 2 (FIG. 1). The dimensions of the saddle assembly 102 are chosen relative to the freeboard of the boat 2 (this freeboard usually being in the range of 3-5 feet for boats used in oceanographic surveying) that when the handling apparatus is in its launch and retrieval position, the apparatus 10 will lie at or slightly below water level. Launching of the apparatus 10 is achieved by moving the piner arms 142 by means of hydaulic piston-and-cylinder assemblies 144 to their unlocked position, so that the apparatus 10 becomes suspended by means of the cable 6. To reduce any sudden shock loading on the cable 6 as the boat 2 moves in response to wave action, the hydraulic cylinders 136 are connected to a hydraulic accumulator (not shown), which acts as a shock absorber to stabilize in the cable by raising and lowering the members 118 and the saddle assembly 102.

As mentioned above, when the apparatus 10 is placed in the water, it will rapidly flood and become heavier than water. The apparatus can thus be lowered to the desired depth simply be reeling out the cable 6 and, once the appropriate length of cable has been played out, towing and surveying can commence. During towing, the rollers 170 prevent excessive lateral movement of the cable 6 relative to the saddle assembly 102, thus preventing the apparatus 10 wandering excessively from side to side of the track of the boat 2. The roller 172 also serves during towing to prevent the cable 6 moving too far rearwardly of the saddle assembly 102, thus preventing potential damage to both the cable and the saddle assembly.

Recovery of the apparatus 10 is accomplished in a manner substantially the reverse of that used to launch the apparatus; during recovery; the rollers 170, 172 and 172' all cooperate in guiding the cable 6 relative to the saddle assembly 102 to prevent damage to the saddle assembly and the cable and also serve to guide the apparatus 10 into the correct position relative to the saddle assembly 102 during the recover operation so that the pincer arms 142 can grasp the cable connection member 100.

Figure 7:
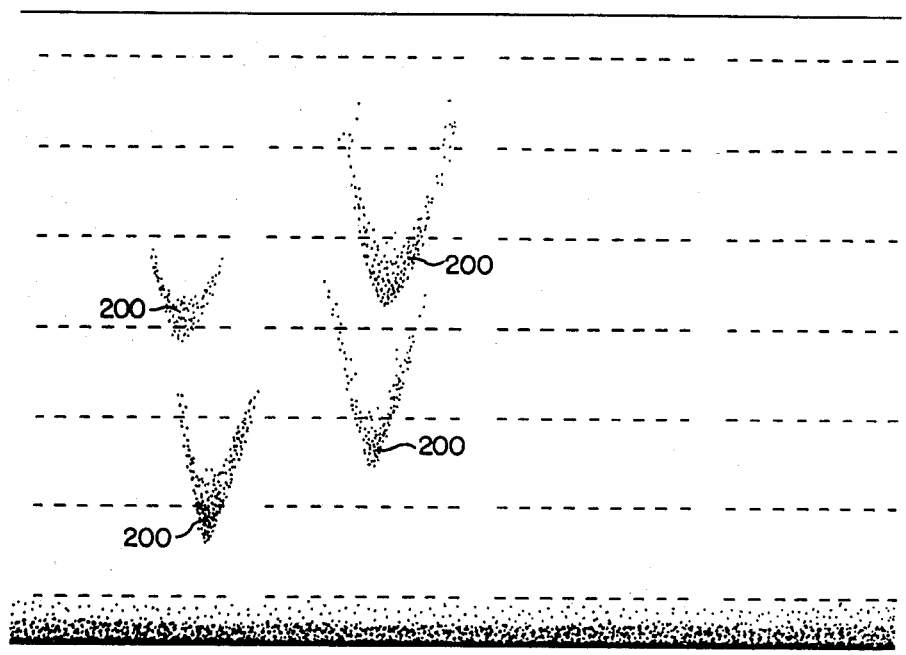
FIG. 7 shows a plot produced using the sonar apparatus shown in FIGS. 1-6 showing the characteristic form of the traces produced by columns of gas bubbles.

The auxiliary apparatus mounted on the boat 2 and used in connection with the apparatus 10 is generally similar in type to that used in connection with conventional oceanographic survey devices. It includes a generator which causes the transducers 70, 72 and 80 to emit pulses of low frequencies sonar radiation and plotters which plot graphs on rectangular axes, one axis representing time and the other axes representing time between the termination of the previous pulse and the returning signal. However, while a conventional downward-looking sonar apparatus only requires one such plotter, three are used in connection with the apparatus 10; one plots the signals received from the transducer 80 and operates in exactly the same manner as that used with prior art sub-bottom profilers, while the other two, which plot the signals received from the transducers 70 and 72 respectively, show the traces received from the starboard and ports sides of the apparatus 10. Part of one of the resultant lateral plots is shown in FIG. 7; this figure shows four of the characteristic smeared parabolic traces 200 indicating bubble columns rising from the ocean floor.

It will be apparent to those skilled in the art that numerous changes and modifications may be made in the specific embodiments of the invention described above without departing from the scope of the invention. Accordingly, the foregoing description is to be construed in an illustrative and not in a limitative sense, the scope of the invention being defined solely by the appended claims.

I claim:

1. In combination, a towable oceanographic device and a towing vessel therefor, said oceanographic device having a fairing and a cable attachment member projecting upwardly from said fairing; said device having a center of gravity and said attachment member being attached to said device and projecting upward therefrom along a vertical line extending through the center of gravity, said towing vessel having mounted thereon a winch and a handling apparatus, said handling apparatus comprising a parallel pair of arms pivotally mounted on said vessel for simultaneous pivotal movement relative thereto about a substantially horizontal axis and a clamping assembly mounted upon said arms at a point spaced from the point at which the arms are mounted on the vessel, said clamping assembly being pivotable relative to said arms about a substantially horizontal axis and being provided with clamping means movable between a locked position, wherein said clamping means clamps said cable attachment member, thereby preventing relative movement between said oceanographic device and said clamping assembly, and an unlocked position, wherein said clamping means does not clamp said cable attachment member, thereby permitting relative movement between said clamping assembly and said oceanographic device;

said vessel also being provided with a cable connected between said winch and said cable attachment member; said winch being mounted to play out cable between and parallel to said arms;

the clamping assembly further including two triangular frames, said frames being attached together in parallel relationship and mounted between and parallel to the two said arms, each frame including a pad mounted parallel with the frame to engage the surface of the fairing when the device is in storage position;

a plurality of rollers mounted between the frames to form an opening to receive and maintain the cable within the opening at all times; and means for guiding the cable from the opening through an arc of about 90° toward said winch, said arc lying in a plane parallel to said arms.

2. An apparatus according to claim 1 further comprising at least one hydraulic piston-and-cylinder device connected between said vessel and said arms for effecting pivotal movement of said arms relative to said vessel.

3. A combination according to claim 2 wherein said clamping assembly further comprises at least one cable stop for limiting movement of said cable relative to said clamping means when said clamping means is in its unlocked position.

4. A combination according to claim 1 wherein said cable guiding means is arcuate in form so that, when said cable attachment member is being clamped by said clamping means, said cable guiding means will guide the portion of said cable adjacent said cable attachment member substantially vertically but will guide a portion of said cable adjacent said arms substantially parallel to said arms.

5. A combination according to claim 4 wherein said cable attachment member has a recess formed therein and wherein said clamping means, when in its locked position, enters said recess.

6. A combination according to claim 5 wherein said clamping assembly further comprises at least one cable stop for limiting movement of said cable relative to said clamping means when said clamping means is in its unlocked position.

7. An apparatus according to claim 6 further comprising at least one hydraulic piston-and-cylinder device connected between said vessel and said arms for effecting pivotal movement of said arm relative to said vessel.

8. An apparatus according to claim 4 further comprising at least one hydraulic piston-and-cylinder device connected between said vessel and said arms for effecting pivotal movement of said arm relative to said vessel.

9. A combination according to claim 1 wherein said cable attachment member has a recess formed therein and wherein said clamping means, when in its locked position, enters said recess.

10. A combination according to claim 1 wherein said clamping assembly further comprises at least one cable stop for limiting movement of said cable relative to said clamping means when said clamping means is in its unlocked position.

* * * * *